(12) United States Patent
Fauquex et al.

(10) Patent No.: US 11,759,383 B2
(45) Date of Patent: Sep. 19, 2023

(54) MOTORIZED EXERCISE DEVICE AND METHODS OF EXERCISE LEARNING

(71) Applicant: LAMBDA HEALTH SYSTEM SA, Yverdon-les-Bains (CH)

(72) Inventors: Aurelien Fauquex, Lausanne (CH); Yannick Charrotton, Echandens (CH)

(73) Assignee: LAMBDA HEALTH SYSTEM SA, Yverdon-les-Bains (CH)

( * ) Notice: Subject to any disclaimer, the term of this patent is extended or adjusted under 35 U.S.C. 154(b) by 1138 days.

(21) Appl. No.: 15/567,127

(22) PCT Filed: Apr. 21, 2016

(86) PCT No.: PCT/EP2016/058839
§ 371 (c)(1),
(2) Date: Oct. 17, 2017

(87) PCT Pub. No.: WO2016/170028
PCT Pub. Date: Oct. 27, 2016

(65) Prior Publication Data
US 2018/0049937 A1 Feb. 22, 2018

(30) Foreign Application Priority Data
Apr. 21, 2015 (EP) .................... 15164418

(51) Int. Cl.
*A61H 1/02* (2006.01)
*G16H 20/30* (2018.01)
*G06V 40/20* (2022.01)

(52) U.S. Cl.
CPC ......... *A61H 1/0266* (2013.01); *A61H 1/0237* (2013.01); *A61H 1/0255* (2013.01);
(Continued)

(58) Field of Classification Search
CPC ...... A61H 1/00; A61H 1/0214; A61H 1/0237; A61H 1/024; A61H 1/0244;
(Continued)

(56) References Cited

U.S. PATENT DOCUMENTS 5,466,213 A * 11/1995 Hogan .................... A61H 1/02
482/901
6,007,500 A * 12/1999 Quintinskie, Jr. ... A61H 1/0281
601/84

(Continued)

FOREIGN PATENT DOCUMENTS

| WO | 2005/074371 A2 | 8/2005 |
| WO | 2013/179230 A1 | 12/2013 |
| WO | 2015/007349 A1 | 1/2015 |

OTHER PUBLICATIONS

Definition of Connect; 2021; Merriam-Webster; https://www.merriam-webster.com/dictionary/connect (Year: 2021) (Year: 2021).*

*Primary Examiner* — Joseph D. Boecker
*Assistant Examiner* — Thomas W Greig
(74) *Attorney, Agent, or Firm* — Robert C. Netter, Jr.; Dann, Dorfman, Herrell & Skillman

(57) ABSTRACT

Exercise robot suitable for rehabilitation and methods of its operation are provided. In particular a method in which the exercise robot learns an exercise movement on the basis of movements conducted by the aid of a human assistant holding the leg of a patient and moving the leg with muscular form to conduct an exercise movement. The rehabilitation robot actively accompanies the exercise movement in an active compliance mode and records the movement so as to determine an exercise movement stored in the control unit of the device. The rehabilitation robot can then produce the determined exercise in an exercise mode.

20 Claims, 2 Drawing Sheets

(52) U.S. Cl.
CPC ......... *A61H 1/0274* (2013.01); *A61H 1/0285* (2013.01); *G06V 40/23* (2022.01); *G16H 20/30* (2018.01); *A61H 1/0277* (2013.01); *A61H 1/0281* (2013.01); *A61H 2201/0173* (2013.01); *A61H 2201/0176* (2013.01); *A61H 2201/0192* (2013.01); *A61H 2201/1215* (2013.01); *A61H 2201/1261* (2013.01); *A61H 2201/1269* (2013.01); *A61H 2201/149* (2013.01); *A61H 2201/164* (2013.01); *A61H 2201/1635* (2013.01); *A61H 2201/1638* (2013.01); *A61H 2201/1642* (2013.01); *A61H 2201/1659* (2013.01); *A61H 2201/1664* (2013.01); *A61H 2201/1671* (2013.01); *A61H 2201/1676* (2013.01); *A61H 2201/5035* (2013.01); *A61H 2201/5061* (2013.01); *A61H 2201/5064* (2013.01); *A61H 2201/5069* (2013.01); *A61H 2201/5084* (2013.01); *A61H 2203/0437* (2013.01)

(58) Field of Classification Search
CPC .... A61H 2001/0248; A61H 2001/0251; A61H 1/0255; A61H 1/0259; A61H 1/0262; A61H 1/0266; A61H 1/0274; A61H 1/0277; A61H 1/0281; A61H 1/0285; A61H 1/02–0288
See application file for complete search history.

(56) References Cited

U.S. PATENT DOCUMENTS

| | | | | |
|---|---|---|---|---|
| 2002/0010056 | A1* | 1/2002 | Borsheim | A61H 3/00 482/54 |
| 2003/0207739 | A1* | 11/2003 | Whitall | A63B 22/205 482/92 |
| 2004/0172097 | A1* | 9/2004 | Brodard | A61H 1/0255 607/49 |
| 2006/0079817 | A1* | 4/2006 | Dewald | A63B 21/4019 482/901 |
| 2007/0027410 | A1* | 2/2007 | Cost | A61H 1/0266 601/24 |
| 2007/0299371 | A1* | 12/2007 | Einav | A63B 21/0058 601/5 |
| 2015/0190200 | A1* | 7/2015 | Courtine | A61N 1/36003 604/20 |
| 2016/0158086 | A1* | 6/2016 | Schmitt | A61H 1/0237 601/27 |

* cited by examiner

MOTORIZED EXERCISE DEVICE AND METHODS OF EXERCISE LEARNING

This application is a § 371 application of PCT/EP2016/058839, filed Apr. 21, 2016, which claims priority to European Patent Application No. 15164418.4, filed Apr. 21, 2015. The entire disclosure of each of the foregoing applications is incorporated by reference herein.

TECHNICAL FIELD

The present invention relates in a general manner to the fields of exercise devices, robotics and rehabilitation. More specifically, the present invention provides a motorized exercise device, methods for operating the exercise device, a method for determining and/or storing an exercise movement in a motorized exercise device, and methods for programming and/or configuring the motorized exercise device. The invention also relates to the learning of a exercise movement by an exercise device.

Background Art and Problems Solved by the Invention

The present invention is generally concerned with developing convenient and therapeutically efficient rehabilitation robots and with providing means of operating such robots in an efficient, convenient and therapeutically personalized manner.

In the field of robotics applied to rehabilitation, powered robotic arms are used reproducing physiological articular trajectories and taking over or simulating the segmentary charges of a movement. The robotic arms contain an articulated, mechanical system, which is in some manner connected to a human subject and which is capable of conducting movements in a determined manner for the purpose of exercising. Depending on how motors act upon the articulated system, one can distinguish serial, parallel and hybrid devices. In the latter, motors are partially constructed in series and partially in parallel for acting on the articulated system and finally thereby on a limb of a human subject.

Currently, powered robotic arms for re-education of the lower limbs are generally serial, exoskeleton-based structures, such as the MotionMaker™. These devices are based on an exoskeleton fixed along the lower limbs of an individual, wherein a series of actuating motors cause movement of the exoskeleton and of the limbs attached thereto. An example of a serial, hip-knee-ankle exoskeleton-based device is disclosed in EP 1 387 712.

A hybrid system containing parallel powered orthoses having a λ-structure is disclosed in WO2015/007349. In the devices disclosed in this document, two parallel motors act upon an articulated system having a lambda configuration, and a further motor is acting in series on a rotational position of a contact plate, providing the possibility of adjusting the orientation of the foot or of a hand, for example. WO2015/007349 discloses advantages of substantially parallel systems such as the lambda system compared to the exoskeleton-based structures.

A further manner of distinguishing exercise robots suitable for rehabilitation is by reference to the manner by which a human patient interacts with the articulated system. In exoskeleton-based structures, the limbs are generally fixed at several positions between articulations to the articulated system, the latter thereby constituting the exoskeleton, wherein a movement of the articulated system is synchronously followed by the limb of a patient fixed to the exoskeleton. On the other hand, end-effector devices fix on one contact point or area of the patient, generally the extremity of a limb, such as the foot or hand, and the limb can be mobilized in an exercise by the robot displacing the position and/or orientation of the end-effector position, which is also referred to as tool center point (TCP). The lambda-system WO2015/007349 is an end-effector device, but various serially-powered articulated systems can, in principle, also be conceived as end-effector devices.

One purpose of a rehabilitation robot is to mobilize a limb that a patient cannot mobilize with his or her own muscular force alone, or that a patient cannot mobilize to an extent that would be sufficient for preventing drastic loss of muscular status of the limb or for rehabilitation in general. In all types of rehabilitation robots, the anthropometric parameters of a human subject to be exercised have to be taken into account when determining parameters of exercising movements, such as speed, acceleration and trajectories. Examples of important anthropometric parameters in the context of rehabilitation, for example, are the lengths of limbs and the lengths between articulations of a limb. For example, a patient having longer legs may conduct a movement having a longer trajectory than a patient having short legs, and a patient having longer thighs may conduct a different exercise trajectory than a patient having longer shin length with identical leg length, for example. Using suitable algorithms, the central data processing system of a rehabilitation robot can determine appropriate exercise movements on the basis of the anthropometric parameters and selected exercise types. It is also noted that the central processing unit may use algorithms for modelling some anthropometric parameters, such as the weight of a leg, on the basis of some key anthropometric parameters that are easy to measure. It is noted that in many exoskeleton based devices, mechanical adjustments to the robotic arms may need to be made for adjusting the device to the anthropometric parameters of a human individual.

However, in spite of using personal anthropometric parameters for determining exercises of a human subject, the algorithmically determined exercise parameters may not be entirely satisfactory for the subject. Indeed, the algorithm may not take into account all the particularities of a human subject that determine an ideal exercise movement.

It is thus a particular objective of the present invention to provide a way of improving and/or further personalizing the determination of exercise parameters. In particular, it is an objective of the invention to define exercises that are particularly adapted to an individual human subject.

It is another objective of the invention to "teach" a suitable, personalized exercise movement to a motorized rehabilitation device, in a manner enabling the device to reproduce the movement or to determine a personalized exercise movement.

It is also an objective of the invention to facilitate the operation of a rehabilitation robot, to facilitate the programming of exercise movements and to facilitate the programming of personalized exercise movements adjusted to an individual human subject. In case of human patients, an exercise robot is generally operated by an assistant, who may be a therapist, such as a physiotherapist, a nurse or a doctor. It is an objective of the invention to provide a way of allowing the assistant to define a personalized exercise movement to be conducted by a exercise robot, and to facilitate and improve the implementation of highly personalized exercises by an exercise robot.

In the field of rehabilitation robots, the programming of a particular exercise, for example, the definition of a particular, complex exercise trajectory is very difficult and a time extensive task. It is thus an objective of the invention to rapidly program exercises in a rehabilitation robot.

Furthermore, the exercises of rehabilitation robots are generally programmed by programmers, who do generally not have a particular feeling for or understanding of the forces and/or torque that are experienced by a human subject nor of the forces and/or torque a particular human subject can support without stress or damage to the musculoskeletal system.

It is noted that rehabilitation robots are suitable for conducting physical exercises for human subjects suffering from impairment of the motor function, such as hemiplegia, paraplegia or tetraplegia patients, for example. However, human subject having other medical conditions and even healthy humans may also use the motorized exercise device of the present invention.

The present invention addresses the problems depicted above.

SUMMARY OF THE INVENTION

Remarkably, the present inventors provide a motorized exercise device comprising an articulated system for conducting exercise movements and comprising a control unit configured to record an exercise movement conducted by a human subject directly or with the aid of an assistant. The present invention concerns methods of learning exercises by the exercise device.

In an aspect, the invention provides a computer-controlled, motorized exercise device comprising an articulated system for conducting exercise movements and at least one interface for connecting a limb of a human subject to said articulated system.

In an aspect, the invention provides a computer-controlled, motorized exercise device comprising an articulated system for conducting exercise movements, motors for acting on and/or propelling said articulated system, wherein said articulated system comprises at least one interface for attaching a limb of a human subject, wherein said exercise device comprises a measuring system for determining torque and/or force, in particular at said interface, and a control unit configured to control a movement of said articulated system by controlling said one or more motors.

In an aspect, the invention provides a computer-controlled, motorized exercise device comprising; one or more motors; an articulated system for conducting movements under the activity of said motors, the articulated system comprising at least one interface for connecting said articulated system to a limb of a human subject; a measuring system configured to measure torque and/or forces generated by the limb of a human subject at said interface; and a control unit configured to control a movement of said articulated system by controlling said one or motors.

In an embodiment, the control unit of said computer-controlled, motorized exercise device is configured to operate in a mode of active compliance, in which said interface actively accompanies a movement of said limb under the effect of said motors; wherein, in said mode of active compliance, said control unit determines a movement of said articulated system as a function of parameters including torque and/or force measured by said measuring system, in particular by a torque and/or force sensor. In an embodiment, in said mode of compliance, a movement of said articulated system accompanying said movement of said limb is controlled by said control unit to be conducted in a manner so as to avoid any resistance by said articulated system to a muscle-propelled movement of said limb connected to said interface.

In an embodiment, the control unit is configured to conduct said accompanying movement by: measuring forces and/or torque by said torque and/or force sensor; determining the extent to which said force and/or torque are caused by a muscle-propelled movement of said limb; determining a movement and/or new position of the interface that is suitable to avoid force and/or torque caused by the muscle-propelled movement at the interface; send instructions to the motors so as to cause the articulated system to conduct said movement suitable to avoid force and/or torque caused by the muscle-propelled movement, thereby actively accompanying said muscle-propelled movement.

In an embodiment, the control unit is configured to record a movement of said articulated system accompanying said movement of said limb in said mode of compliancy, to determine a personalized exercise movement on the basis of the recorded movement and to actively produce said personalized exercise movement in an exercise mode.

In an aspect, the present invention provides a method for operating the computer-controlled, motorized exercise device of the invention, the method comprising the step of recording a movement of said interface in an active compliance mode, in which the articulated system follows and/or accompanies a movement of a human subject acting on said interface.

In an aspect, the invention provides a method for determining or programming a personalized exercise movement in a computer-controlled, motorized exercise device, the device comprising a control unit, an articulated system for conducting exercise movements and one or more motors arranged to act on said articulated system under the control of said control unit, wherein said articulated system comprises an interface for connecting the articulated system to a limb of a human subject, and wherein said exercise device comprises a measuring system for determining torque and/or force at said interface, the method comprising the steps of:

determining forces and/or torque at said interface by way of said measuring system while a muscle-propelled movement is conducted acting on said interface;

actively accompanying said muscle-propelled movement by said motors acting on said articulated system, wherein said control unit determines the parameters of an active accompanying movement of said articulated system on the basis of the measurements of forces and/or torque by said measuring system;

recording the said active accompanying movement;

determining a personalized exercise movement on the basis of the recorded active accompanying movement.

In an aspect, the invention provides a method for storing a personalized exercise movement in a control unit of the computer-controlled, motorized exercise device of the invention, the method comprising the steps of:

placing the human subject in an exercise position with respect to the device and connecting the limb of the human subject with said interface;

conducting a muscle-propelled movement with the limb;

measuring forces and/or torque at said interface by way of said measuring system during the step of conducting said muscle-propelled movement, and;

actively accompanying said muscle-propelled movement by one or more motors acting on said articulated system, wherein said control unit determines the parameters of an active accompanying movement of said articulated system on the basis of measurements of forces and/or torque by said measuring system;

recording the said active accompanying movement by the control unit, thereby storing a personalized exercise movement into the control unit of said exercise device.

In another aspect, the invention provides a method for programming and/or configuring a computer-controlled, motorized exercise device of the invention, the method comprising steps of the methods of the invention.

In yet another aspect, the invention provides methods for teaching a computer-controlled, motorized exercise device an exercise movement, the methods comprising steps of the methods of the invention.

In some aspects, the invention provides a method of learning an exercise movement by or in a exercise device, the method comprising the steps as the method for determining an exercise movement or the method storing a personalized exercise movement in a control unit of the computer-controlled, motorized exercise device.

In some aspects, the method encompasses a method of teaching an exercise movement a computer-controlled exercise device. The teaching is conducted by a human assistant operating a device of the invention.

The methods of the invention are generally learning methods, in which an exercise device learns an exercise movement conducted by a human subject or a human assistant, the device being capable of reproducing the exercise or of determining a personalized exercise on the basis of the recorded movement. The human subject or a human assistant appears as a teacher, and the exercise device is capable of producing exercises on the basis of the exercises taught by the human.

In an aspect, the invention provides a computer-controlled, motorized exercise device configured to enable, execute and/or conduct any one of the methods of the invention.

In a preferred embodiment, the exercise device of the invention is a rehabilitation device, in particular a rehabilitation robot.

In an aspect, the invention provides the use of the computer-controlled, motorized exercise device for teaching and/or programming exercise movements.

In an aspect, the invention provides a method for conducting exercise movements, the method comprising the step of producing exercise movements stored, determined, programmed, taught and/or configured in accordance with the methods of the present invention.

Further aspects and preferred embodiments are provided herein below, in the remainder of this specification and in the appended claims.

In the detailed description herein below, reference is made to the drawings for referring to particular embodiments and for illustrating the present invention.

DETAILED DESCRIPTION OF THE PREFERRED EMBODIMENTS

The present invention relates to a motorized, computer controlled exercise device that is particularly suitable for rehabilitation purposes. Such devices are frequently called rehabilitation robots. The exercise devices are preferably adapted or suitable for conducting physical exercises with human subjects suffering from impairment of their motor functions, such as hemiplegia, paraplegic and tetraplegic patients. The exercise device is also suitable for elderly persons or persons requiring physical exercising and/or stimulation of the musculoskeletal system for any reason. Accordingly, the exercise devices of the invention are preferably configurable to be used for physical exercising of human subjects in general and are not limited to rehabilitation and/or therapeutic exercises. In another embodiment, the device of the invention is not a rehabilitation device, but a exercise device that can be used by healthy subjects for the purpose of improving fitness, for example.

Figure 1:
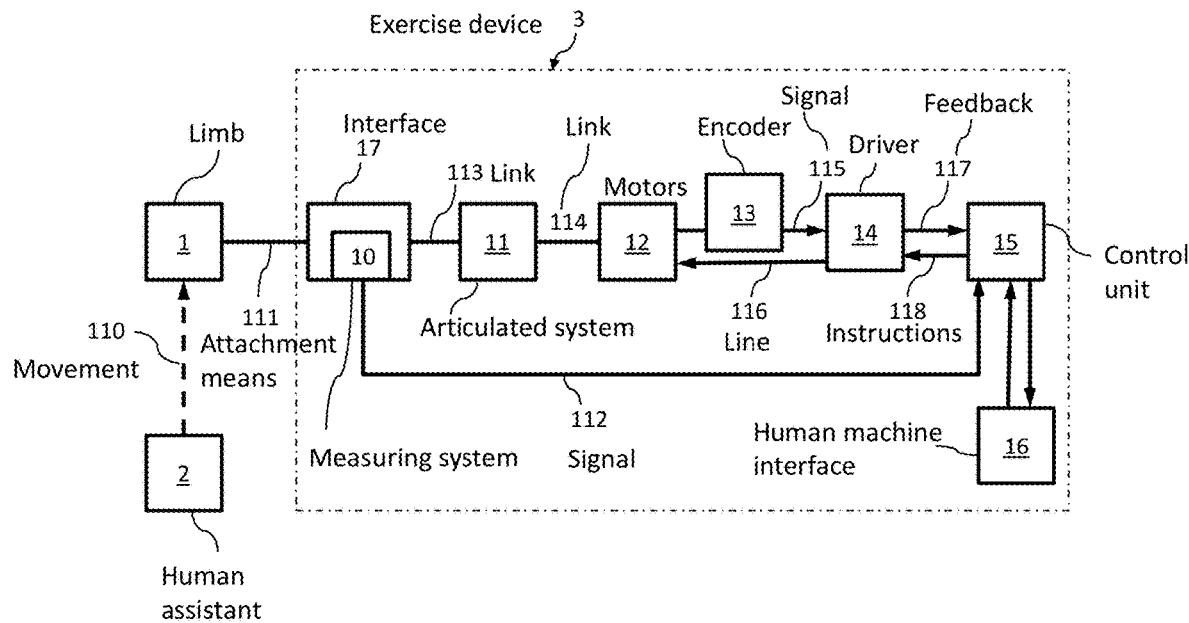
FIG. 1 schematically illustrates a computer-controlled, motorized exercise device in accordance with an embodiment of the invention.

FIG. 1 schematically illustrates the general construction and operation principle of a computer controlled exercise device 3 according to an embodiment of the invention. The device 3 comprises an interface 17 where it interacts physically with a human subject. The device 3 may generally correspond to the devices disclosed in WO2015/007349 or possibly also in the serially constructed, exoskeleton-type device disclosed EP1387712.

For the purpose of the present specification, the term "comprising" is intended to mean "includes, amongst other". It is not intended to means "consists only of".

The interface 17 is adapted to accommodating a human limb 1 that can thus be connected at the interface 17. In a preferred embodiment, the interface 17 is adapted to be attached with the extremity of a human limb 1, such as the foot or hand of a human subject, for example. In particular, the interface 17 is adapted to accommodate a part of a limb 1, preferably the distal part or end of a limb 1. For example, the interface 17 may be a podal interface, for example in the form of a pedal, to which the foot of a human subject can be attached.

The interface 17 preferably contains attachment means 111, for example straps, belts or other releasable fixation means for attaching a limb 1 to the interface 17. When the limb is attached to the interface 17, it is preferably connected in a temporarily fixed manner, so that the limb remains permanently attached during an exercise or during the methods of the present invention. The limb 1 may be detached from the interface 17 once an exercise is terminated or the method of the invention has been completed, for example. The device preferably comprises a releasable attachment means for attaching the distal extremity of a limb 1 to the interface 17.

In an embodiment, the device of the invention comprises only one interface 17 per limb 1, and thus only one attachment means per limb. For example, only the foot of a leg is attached or only the hand of an arm. This embodiment is in line with end-effector devices, in which the exercise device is configured to act only at one interface with a limb of the human subject. There are two interfaces 17 if exercises are conducted with two limbs. In this manner, disadvantages of fixing successive segments of a limb are avoided. An advantage of end-effector type devices is that they leave more freedom for articulations of a human subject during exercising, reducing the occurrence of potentially undesired forces on the articulations.

In some embodiments, the interface 17 may be referred to as a tool center point (TCP). The term TCP expresses more specifically that the interface 17 defines an entity the position and/or orientation of which is the center or focus point of the devices robotic activities. The activity of the motors has the purpose of defining the position and orientation of said TCP and/or interface 17. The term TCP is particularly applicable to end-effector type devices in accordance with preferred embodiments of the invention.

The device 3 further comprises an articulated system 11, which provides or defines the mobility of the interface 17. The interface 17 may be considered to be part of the articulated system 11 or may also be considered as a separate element that is connected mechanically by link 113 to the articulated system 11. The articulated system 11 defines the positioning and orientation of the interface 17 in the space. The articulated system 11 and the interface 17 may also be referred to as "robotic arms" 11. The nature of the articulated system, in particular the types and nature of articulations contained also determine the position and/or orientations the interface 17 may take, as well as the trajectories that the interface may conduct. Importantly, the articulated system 11 is preferably constructed so as to enable different trajectories and thus different exercise types, such as cycling and pushing, for example. The capacity of the articulated system to define different trajectories makes it possible to define personalized exercises that are adapted to a particular human subject, and to take the anthropometric parameters of the human subject into account.

The combination of interface 17 and articulated system 11 may be considered as an orthose. If one includes motors and possibly motor drivers, one obtains a powered orthose.

The device 3 further contains one or more motors 12 for acting upon and/or propelling the articulated system 11. The motors 12 may be selected from all types of electric motors and all types of actuators, for example. In an embodiment, the device 3 comprises a plurality of electric motors, for example 2-10, more preferably 2-5, for example 3-4 electric motors per articulated system. Reference numeral 114 indicates the mechanical link and interaction between the motor 12 and the articulated system 11. As has been mentioned elsewhere, the present invention encompasses devices in which a plurality of motors are configured in series, in parallel, or as a hybrid device comprising a combination of motors some of which are working in series and in parallel on the articulated system.

At this position, it is noted that the device of the invention preferably comprises two articulated systems 11, allowing exercising two limbs, at the same time, for example both legs or both arms. In this case, the device comprises also two interfaces 17 for attaching each of the two limbs of the subject 4, each articulated system being equipped with its own interface 17 and, accordingly, its own measuring system 10. If there are two articulated system, each of them can preferably independently propelled and thus comprises its own motor or motors 12. In the following, the invention is discussed at the example of one articulated system only, even though exercises may involve both articulated system. Interestingly, the steps associated with the learning of an exercise movement by the device of the invention are preferably accomplished with one limb 1 only and thus with one articulated system at a time.

The device 3 of the invention preferably comprises a control unit 15, for example a computer, for controlling the activity of the one or more motors 12. Typically, the control unit 15 sends instructions 118 to a motor driver 14, which powers the motor 12 via line 116 as required for achieving a movement that is intended to be conducted by the articulated system 11. On the other hand, an encoder 13 is used to provide a feedback about the actual position of the motor 12. For example, if the motor 12 is an electric motor comprising a rotating shaft, the encoder 13 is preferably adapted to send a signal 115 corresponding to an angular position of the motor 12 to the driver 14. The driver also produces feedback 117 to the control unit 15 with respect to the position of the motor 12. In this manner, the driver 14 constantly compares a target motor position with an actual position provided by the encoder 13, thereby allowing the device to move the articulated system 11 and finally the interface 17 in a controlled manner. The "motor positions", for example angular positions of the motor 12, determine the position and orientation of the interface 17.

The device 3 further preferably comprises a human machine interface (HMI) 16. The HMI is used by a human operator or assistant for operating the device 3. For example, the HMI is used for selecting particular exercises, exercise parameters and/or for entering anthropometric data concerning an individual human subject. The control unit 15 preferably contains algorithms and models taking the anthropometric parameters into account for calculating exercise movements. Furthermore, the control unit 15 contains programs for assuring the safety of the device during operation. The HMI 16 may also be used for instructing the device to select one out of a plurality of available exercises and to switch between exercise modes and learning modes. The present invention is particularly concerned with a learning mode, in which the device 3 determines and stores a particular exercise movement on a memory space of the control unit 15.

The device of the invention preferably comprises a measuring system 10 for determining torque and/or force. In a preferred embodiment, the measuring system is arranged so as to be suitable for the determination of forces and/or torque at the interface 17. The measuring system 10 produces a signal 112 that can be used by the control unit 15 for determining forces and/or torques at the interface 17. More specifically, the measuring system 10 is suitable for determining the force and/or torque exerted by the limb 1 of the human subject at the interface 17, in particular by the distal end of the limb 1, for example by a foot in contact with an interface 17 in the form of a foot plate.

One purpose of the measuring system 10 is to measure forces and/or torques at the interface 17, while a muscle-propelled movement is conducted acting on said interface 17. In addition, in some embodiments, the method may comprise a step of conducting a muscle-propelled movement.

The expression "muscle-propelled movement" here means any movement that is caused by muscular force. The expression "muscle-propelled movement" is thus used to distinguish the movement from movements that are propelled by motors of the device.

In accordance with the present invention, the muscle-propelled movement may be conducted by a human subject placed in an exercise position with respect to the device, if the human subject is capable of performing such movements. If the human subject has impaired motor and sensory function, such as a paraplegic or tetraplegic patient, the muscle-propelled movement is conducted by a human assistant holding the limb 1 in his hands and acting with the assistant's muscular force on the limb 1. The limb that is moved by the assistant in turn exerts forces and/or torque at said measuring system 10. In this case, the muscular force of said muscle-propelled movement stems from the assistant's muscles. The movement of the human subject's limb by the muscular force of an assistant is a preferred embodiment of the invention.

In an embodiment, said muscle-propelled movement is a movement 110 conducted by a human assistant 2 holding a limb 1 connected to said interface 17 and moving said limb 1 with his or her hands so as to conduct said muscle-propelled movement. In this embodiment, the muscle-force propelling the muscle-propelled movement thus stems from the human assistant.

The muscle-propelled movement produces an "input" at the measuring system 10 that is used by the control unit 15 for determining an active accompanying movement, as will be discussed in more detail elsewhere in this specification.

In an embodiment, said measuring system for determining torque and/or force at said interface 17 is selected from a force and/or torque sensor and from a combination of one or a plurality of sensors configured to enable the determination of force and/or torque. For example, two sensors, a torque sensor and a force sensor may be used, or a combined force and torque sensor. Various combinations are envisaged by the invention. For example, a single sensor capable of measuring forces and torque may be used. Such a sensor may, for example, measure force and torque on two or on three axes of space, respectively, such as Fx, Fy, Mx and My, or Fx, Fy, Fz, Mx, My, and Mz, for example. In a preferred embodiment, the measuring system measures at least forces on two axes and torque on one axe (Fx, Fy, Mz). Since a six-axis force and torque sensor is relatively expensive, the measuring system may comprise separate force sensors and torque sensors that are suitable for producing the signals required for a respective embodiment.

The number of axes to be covered by one or more force and/or torque sensors generally depends on the articulated system and the degrees of freedom provided by said articulated system. Preferably, the measuring system 10 is suitable to determine forces exerted on the axis on which the articulation provides a degree of freedom. Similarly, the measuring system 10 is preferably suitable to determine torque of the axis where there is a degree of freedom, preferably on an axis corresponding to an axis of rotation. An exemplary training device for training lower limbs typically covers two axis of freedom defining a plane providing mobility to the knee and hip articulations plus a rotational axis providing mobility for the ankle around an axis that is perpendicular to the plane. In such a system, one or more sensors for measuring at least forces along two axis (Fx, Fy), and torque of the rotational axis (Mz) would be preferable, although measuring forces and/or torque on other axis is not excluded and may provide further data that could be relevant with respect to safety of the device, for example.

Instead of one or more force and/or torque sensor, the measuring system 10 may contain any equipment that is suitable to determine force and/or torque at the interface 17.

Preferably, the measuring system 10 is directly associated at and/or in connected to the interface 17, such that force and/or exerted by the limb 1 at the interface 17 can be directly and readily determined. Preferably, the measuring system is mechanically and/or functionally associated with the interface so as to determine forces and/or torques exerted upon the interface 17.

As has been mentioned previously, the interface 17 preferably comprises an attachment arrangement 111 for attaching a limb 1, preferably at the distal extremity of the latter.

Once the limb 1 is attached in this manner, any movement exerted by the limb 1 acting on the interface 17 will result in a signal produced by the measuring system 10. Even a non-moving limb 1 attached to the interface 17 will generally produce forces and/or torque that can be sensed by the measuring system 10, for example due to the gravity of the limb 1 or the flexion of the limb 1 or due to other parameters, which may have anthropometric or biological causes.

Since the limb 1 is attached to the interface 17, forces and/or torque can in principle be determined for any direction encompassed by the measuring system, including flexion and stretching of the limb, pushing the limb, raising the limb, and so forth. For example, forces and/or torque may be determined with respect to movements in which a limb 1 pulls at the interface 17 or in movements in which a limb pushes on the interface 17, or in which a limb 1 changes orientation. It is noted that the attachment means 111 for attaching the limb 1 may also be mechanically and/or functionally connected to the measuring system 10, such that forces/torque acting on the attachment means can also be measured. In this regard, the attachment means for attaching the limb 1 may be considered as part of the interface 17.

The exercise device is preferably operational in various different configurations, such as different operational modes. Examples of such modes are the exercise mode, recording mode, active compliance modes and a gravity compensating mode. Some modes may be combined and run at the same time, such as the active compliance mode may be activated at the same time as the gravity compensating mode and the recording mode. Some modes may also require two modes or process steps to occur simultaneously. The learning mode, for example, requires the device to be in an active compliance mode and at the same time in a recording mode. On the other hand, some modes cannot be run simultaneously, such as the exercising mode and exercise learning in the active compliance mode. Features of these operation modes will be described in more detail at various positions in the present specification.

The "exercising mode" or "exercise mode" encompasses in particular exercise movements conducted be the exercise device 3 by acting in a determined, calculated manner on the motors 12. The exercise mode can also be considered as a therapy mode, since the exercises conducted by the device in an exercise mode may be therapeutic exercises. For the purpose of this specification, exercising is physical exercising.

From the viewpoint of the human subject, the device 3 enables passive and active exercising. In passive exercising, the human subject does not apply own muscular force, and the device moves the interface 17 with the sole force of the motors at a defined trajectory. In active exercising, the patient uses at least partially his/her muscular force for exerting forces on the interface 17 and causing it to move along a defined, fixed exercise trajectory.

The passive exercising mode is particularly configured for the training of human subjects suffering from impairment in motor function of their limbs, such as a hemiplegia, paraplegia patient or tetraplegia patient. In this case, the force for the movement of the interface 17 along a particular exercise trajectory stems from the device. The parameters of the exercise, such as the trajectory, speed and accelerations, are predefined, and the human subject "passively" exercises in that his or her limbs are moved by the device in accordance with the parameters of a particular programmed exercise that was selected by a human assistant in accordance with the patient's needs.

The active exercise mode, in turn, is adapted for human subjects who have not lost or not entirely lost motor function of their limbs and can thus conduct exercises with own muscular force. In this type of exercising mode, the exercise device 3 may provide an exercise-dependent and adjustable resistance to a movement conducted under the muscular force of a human subject along a defined exercise trajectory. The resistance is provided by the motors 12, which determine the extent of the force required for moving the articulated system by the human subject. While the exercise device is preferably suitable to be used for this type of active exercises, the main focus of the present invention is on the teaching of exercise movements to the exercise device, so that the exercise device can subsequently perform learned exercises in an exercising mode that allows a human subject to passively exercise.

In an embodiment, the exercise device 3 enables the human subject to perform exercising of the limbs in accordance with rehabilitation and therapy, for example.

The device of the present invention preferably comprises an active compliance mode. The active compliance mode enables the articulated system 11 to actively accompany any movement of the limb 1, for example the muscle-propelled movement of the limb in accordance with an embodiment of the present invention. In the active compliance mode, the articulated system follows and/or accompanies a movement of a human subject acting on said interface 17.

In an embodiment, said step of actively accompanying said muscle-propelled movement is conducted in said active compliance mode, in which said control unit 15 determines a movement of said articulated system 11 that is suitable to avoid, that is, flee, the occurrence of torque and/or force at said interface 17 caused by said muscle-propelled movement. In said mode of compliance, said control unit determines a movement of said articulated system as a function of parameters including torque and/or force measured by the measuring system 10. Said step of actively accompanying said muscle-propelled movement is conducted by the device.

The control unit preferably controls a movement of the articulated system 11 in a manner so as to avoid any resistance by said articulated system 11 to a muscle-propelled movement of said limb 1 connected to said interface 17. The occurrence of resistance is preferably determined on the basis of measurements of said measuring system 10.

In the active compliance mode, the articulated system 11 including the interface 17 moves under the activity of the motors 12 controlled by the control unit 15 without imposing any force or torque on the limb 1, except forces and/or torque required for maintaining the limb 1 in a given position against the effect of gravity, in case this is desired. The active compliance mode may operate with or without gravity compensation, as will be discussed elsewhere in more detail.

Since the device does not exert any forces on the limb 1 in the active compliance mode, this mode is sometimes also considered a transparency mode. The fact that no forces/torque are exerted on the human subject renders the device subjectively "invisible" in terms of forces and/or torque, compared to a typical exercise mode, where the device conducts exercise movements by acting on the limb 1 and forcing it to follow the exercise movement. To put it in simple words, in the active compliance mode, the articulated system 11 follows a movement of a limb 1 in a manner similar to a shadow or a mirror image following its original.

The active accompanying movement in the active compliance mode is controlled by the control unit 15 on the basis of the signals received from the measuring system 10. The control unit 15 preferably determines movements of the articulated system 11 such that the movement clears and/or balances the force and/or torque as measured by the measuring system 10, by moving in a position where the force and/or torque exerted by the limb 1 (due to the muscle-propelled movement) is minimized. It is thus clear that any movement of the articulated system 11 and/or the interface 17 in the active compliance mode is conducted actively by the motors 12 in accordance with instructions received from the control unit 15. The movement of the articulated system in this mode is not a passive reaction in which the articulation concedes to forces exerted by an active movement of the limb 1. In the active compliance mode, the articulation and/or the interface 17 is moved actively by the motors so as to avoid the occurrence of resistance to the muscle-propelled movement of the limb 1.

Assuming the limb of a healthy person is connected at the interface 17 and the person is pushing with muscular force of the limb thereby creating forces and/or torque at the interface 17, the active compliance mode causes the motors to move the articulated in an anticipating manner, in which the movement of the articulated system 11 and the interface 17 is computed on the basis of the data received from the measuring system 10. The anticipating way of determining the trajectory of the articulated system 11 is responsible for the active, motor-propelled movement of the articulated system 11, which movement is thus not a passive movement that is propelled by the muscular force of the limb acting on the interface 17. Ideally, the subject does not feel any resistance from the device to the movement of the limb by way of muscular force.

In an embodiment of the invention, the following steps are preferably conducted by the control unit 15 to conduct the accompanying movement:

measuring forces and/or torque by said torque and/or force sensor 10;

determining the extent to which said force and/or torque are caused by a muscle-propelled movement of said limb 1;

determining a movement and/or new position of the interface 17 that is suitable to avoid force and/or torque caused by the muscle-propelled movement at the interface 17;

send instructions to the motors 12 so as to cause the articulated system 11 to conduct said movement suitable to avoid force and/or torque caused by the muscle-propelled movement, thereby actively accompanying said muscle-propelled movement.

In said active compliance mode, said control unit 15 is preferably configured to conduct the steps above.

The step of determining the extent to which said force and/or torque are caused by a muscle-propelled movement of said limb 1 includes determining of "baseline" forces and/or torque that would be measured in the absence of any muscle-propelled movement of said limb 1, for example due to gravity or anthropometric reasons, and to deduct said baseline forces and/or torque from the actually measured forces and/or torque.

The step of determining a movement and/or new position of the interface 17 that is suitable to avoid force and/or torque caused by the muscle-propelled movement preferably involves the determination of parameters such as the direction, acceleration and/or speed of a movement that is suitable to avoid force and/or torque caused by the muscle-propelled movement. For example, a new position is determined and the parameters of the movement (trajectory, acceleration, speed) into the new position.

Figure 2:
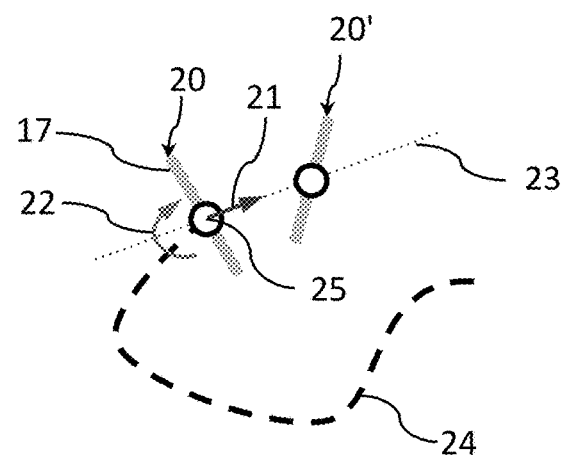
FIG. 2 schematically illustrates the control of the movement of an articulated system of an exercise device in an active compliance mode in accordance with an embodiment of the invention.

FIG. 2 illustrates the functioning of the active compliance mode. In this figure, the interface 17 is a foot pedal shown in a first position 20 and a second position 20'. In the first position, the measuring system (not shown) produces signals that are used to determine force 21 and torque 22 exerted on the pedal. Reference numeral 25 indicates the rotation axis of pedal 17. On the basis of force and/or torque at the pedal, the control unit 15 determines a next or second position 20' of the pedal as well as the parameters of the movement to said second position, such as direction, speed, acceleration, for example. The dotted line 23 indicated the calculated direction for moving from the first to the second, next position 20'. The dashed line 24 illustrates the trajectory that the pedal 17 was performing before arriving at position 20.

The "trajectory" can in principle be any course of the interface 17 in space, for example within a plane. The trajectory may be determined as a succession of positions in space and the parameters determining the displacement from one position to the next position. The term "position" preferably not only includes position within space, but also a rotational position or orientation within a point in space. Depending on the degrees of freedom provided by the articulated system, the trajectory may be a succession of positions and orientations in a three-dimensional space or only in a plane.

While the term "trajectory" more specifically refers to positions and orientation of the interface 17 in space, the term "movement" may encompass additional parameters of movement, in particular speed and acceleration. The term acceleration also encompasses deceleration for the purpose of this specification.

In the embodiment shown in FIG. 2, the positions 20, 20' of the interface 17 are defined by the punctual position in a plane corresponding to the plane of the figure, as well as by the rotational position of the pedal on an axis of rotation 25 that is perpendicular to the plane. The rotational position or orientation of the pedal is thus also part of the overall position 20' as determined by the control unit 15.

In accordance with the above said with respect to the active compliance mode, the movement of the articulated system from position 20 to position 20' is preferably propelled by the force of motors 12 of the device 3 and the parameters of the movement are calculated on the basis of forces and/or torque measured by the measuring system 10.

In an embodiment, all movements of said articulated system 11 are active and controlled movements, which are actively conducted by said one or more motors 12 under the control of said control unit 15. This preferably applies to the active compliance mode as well as to an (passive) exercising mode where the human subject does not use own muscular force for performing exercising, for example in case of a patient having impaired motor or sensory function of his or her limbs.

The step of actively accompanying said muscle-propelled movement is controlled on the basis of values at the interface 17 determined by the measuring system 10. This implies that the device does not actively accompany any other movement imposing forces and/or torque on the device of the invention. For example, if the assistant were to push a robotic arm of said articulated system during the active compliance mode, the device would actually prevent any movement of the articulated system due to external forces.

The above said makes clear that the control unit 15 prevents, counteracts and/or bocks any movements of the articulated system 11 originating from forces other than those measured by the measuring system 10 in the frame of a regular operation of the active compliance mode. For example, if one were to push anywhere on the articulated system 11 (other than at the measuring system 10), the articulated system will not move. In other words, the device 3 does not actively accompany any movement imposing forces and/or torque on the device other than the movements resulting in signals produced by the measuring system 10.

If required, the control unit 15 actively counteracts, by instructing the motors 12, any external forces that are not measured at the measuring system 10. Force and/or torque that is in any way sensed or experienced by the device but not detected by the measuring system 10 is suspected to be the result of erroneous use of the device or of an erroneous, potentially dangerous event, and may entail the triggering of a safety procedure, in which any further movement of the articulated system is blocked.

As will be discussed in more detail elsewhere, the invention encompasses different types of active compliance mode, in particular a first mode as described above, and a second mode, where a particular trajectory is fixed, and the active accompanying movement of the articulated system allows the human assistant to determine other parameters of the movements, such as speed and acceleration, for example.

The device of the invention generally takes its own gravity into account in that it carries and/compensates its own weight. The interface 17 is generally kept at a determined position or moved along a trajectory while avoiding any deviating movement due to the gravity of the articulated system or other components of the device.

Accordingly, in an embodiment, exercising device 3 and/or said control unit 15 is configured to compensate gravity of said articulated system 11 so as to keep said interface 17 at a fixed position and/or orientation in the absence of force and/or torque at said interface as determined by said measuring system for determining torque and/or force 10.

In particular, control unit 15 is configured to compensate gravity of said articulated system 11 so as to keep said interface 17 at a fixed position and/or orientation in the absence of force and/or torque due to a muscle propelled movement at said interface 17 as determined by said measuring system 10. If the articulated system 11 and therefore, also the interface 17 are stopped in a particular position, the gravity compensation implies that the motors of the device maintain the position by not rotating (in case of rotating motors), and may thus brake any movement that may be caused by gravity of the device itself or its components.

In addition to the above, the device of the invention may be configured to compensate or not the additional gravity acting on the interface 17 due to the limb 1 attached at the interface. These options apply in particular to the active compliance mode, since in the exercise mode the articulated system 11 follows a predetermined, fixed trajectory and thereby generally is configured to automatically compensate gravity of the limb.

If gravity of the limb 1 were not compensated in the active compliance mode, attachment of a limb 1 to the interface 17 would result in a movement dictated by the laws of gravity, unless the limb 1 is maintained by muscular force in a particular position.

In an embodiment, said step of actively accompanying said muscle-propelled movement is conducted in a gravity compensating mode, in which said device 3 supports said limb 1 attached to said interface 17 against the effect of gravity so as to prevent any movement of the limb 1 caused by gravity and/or in the absence of a movement propelled by muscular force.

Gravity compensation in the active compliance mode generally requires the available of anthropometric information pertaining to an individual human subject. In an embodiment, said control unit 15 contains or was configured to contain personal anthropometric data pertaining to said human subject and/or to the limb 1 of said human subject.

In an embodiment, said control unit 15 is configured to determine, on the basis of personal anthropometric data pertaining to said human subject and/or to the limb 1 of said human subject, the forces acting on said sensor 10 in the absence of muscle-propelled movement while said limb 1 is connected at said interface 17.

The control unit 15 preferably comprises algorithms which allow it to determine the forces and/or torque at the interface 17 caused in the absence of any muscle propelled movement. In particular, the control unit 15 is configured to determine a force and/or torque for any position of the interface 17 that is expected due to forces other than muscular force, such as gravity and possibly other mechanical or anthropometric constraints. The amounts of these forces and/or torque generally vary in dependence of the particular position in space of said articulated system 11 and/or said interface 17. In a gravity compensating mode, the force and/or torque measured at the measuring system 10 determined to be due to gravity may be automatically deducted from the actually measured force and/or torque, such that any accompanying movement in the active compliance mode (and gravity compensating mode) accompanies a purposeful, muscle-propelled movement conducted by the human subject or a human assistant holding and moving the limb.

In an embodiment, the control unit 15 is configured to subtract forces acting on said measuring system 10 in the absence of any muscle-propelled movement at any particular position of said articulated system 11 and/or said interface 17 ("baseline forces") when determining parameters of said active accompanying movement of said articulated system 11.

In an embodiment of the method of the invention, said muscle-propelled movement is conducted by a human assistant 2 holding the limb 1 without carrying the weight of said limb 1, the weight of the limb 1 being supported by the device 3 against the effect of gravity. This applies to the gravity compensating mode, where the device 3 carries the weight of the limb 1.

Gravity compensation in the active compliance mode, during the step of recording a muscle-propelled movement, is not in all cases desirable or wished. In some cases, an assistant may prefer to carry the weight of the limb 1 on his own when conducting a muscle propelled movement, such as a manually conducted exercise movement. In a classic therapeutic exercise conducted by a therapist acting on the limb of a para- or tetraplegic patient (in the absence of a rehabilitation robot), for example, the therapist also carries the weight of the limb. During the step of a recording a movement by the device of the invention, the absence of gravity compensation may improve the sensitivity, perception or the "feeling" of the therapist with respect to the movement to be conducted with the limb of the patient.

In consideration of the above, the invention provides an embodiment, which is conducted in a mode in which gravity of said limb 1 is not compensated by the device. In this embodiment, during the method of the invention, the weight of the limb 1 is preferably supported by a human assistant 2 holding the limb 1 and carrying the weight of the limb 1 with his or her muscular force. In other words, the muscular force of the human assistant may "compensate" gravity of the limb if the device 3 is in a mode in which the gravity of the human subject is not taken into account by the device.

In the following, steps of various embodiments and aspects of the methods of the invention are discussed in more detail.

In an embodiment, the method of the invention comprises the step of placing the human subject in an exercise position with respect to the device 3 and attaching the limb 1 of the human subject with said interface 17. In an embodiment, the distal extremity of a limb 1 is connected at the interface 17, such as the foot or the hand, for example. For attaching the limb 1, attachment means 111 are preferably used. Generally, the human subject will be positioned in a chair or possibly in a bed so as to face the articulated system 11. If the human subject is a patient, such as a paraplegia or tetraplegia patient, the positioning of the human subject is generally accomplished by a trained assistant, such as a physiotherapist, who will preferably supervise the exercising or learning and who will operate the device of the invention to this end.

For learning a personalized exercise movement, the device 3 is preferably switched, for example at the human machine interface 16, to the corresponding learning mode. In this regard, the learning mode is a mode in which the device of the invention 3 records a movement of the articulated system 11. In accordance with the invention, the learning and/or recording is conducted in the active compliance mode as described elsewhere in this specification. The device 3 is this preferably configured to record a movement of the articulated system 11 that occurs in the active compliance mode.

The muscle-propelled movement is preferably conducted during said steps of measuring forces and/or torque at said interface 17 and recording the said active accompanying movement.

The method comprises the step of actively accompanying said muscle-propelled movement by aid of one or more motors acting on said articulated system, wherein said control unit determines the parameters of an active accompanying movement of said articulated system on the basis of the measurements of forces and/or torque by said measuring system.

As becomes apparent from the above, the muscle-propelled movement results in changes of the forces and/or torque measured by the measuring unit 10 at interface 17, and, as a consequence of the active compliance mode, the device performs an accompanying movement of the articulated system 11, preferably in a manner such as to produce no resistance to the muscle-propelled movement.

The method further comprises the step of recording the said active accompanying movement of the articulated system by the control unit 15, thereby storing a personalized exercise movement into the control unit of said exercise device.

Once a movement is recorded in the control unit, a first embodiment of the method of the invention is completed as the movement has been stored on a memory of the control unit and can be reproduced in the form of an movement in which the articulated system acts on the limb 1 and thus causes the limb 1 to perform the trajectory of the movement as recorded. The movement as stored in the active compliance mode constitutes a personalized exercise movement that can be conducted by the device.

In the method of the invention, the muscle-propelled movement is conducted, for example, by a human assistant holding the limb 1 of a human subject, the assistant thus being the teacher, conducting the step of "teaching" the device a particular exercise movement, and the device "learning" the movement as taught by the assistant, by recording the movement in said active compliance mode.

To put it in other words, the device 3 uses the signals produced at the measuring system 10 due to the muscle-propelled movement as an input for defining an exercise movement.

Some advantages of the embodiment where a muscle-propelled movement is conducted by a human assistant 2 shall be set out at this position. These advantages may apply in particular to the situation where the human subject is a patient suffering from impairment in motor or sensory function of his and/or her limbs, such paraplegia and tetraplegia patients. The human assistant 2 is generally a trained therapist, such as a physiotherapist, for example. When holding the limb of the patient in the hands, the therapist may conduct a typical, therapeutic movement as if the device of the invention were absent. This is possible due to the active compliance mode, in which the articulated system avoids the occurrence of resistance to the muscle-propelled movement by the articulated system and/or interface 17. The therapist thus teaches the device (or inputs) a movement that the therapist would perform together with the patient alone, in a personalized manner, in the absence of any rehabilitation robot. This movement is part of a typical therapeutic movement of a therapist with the patient, if conducted for a longer time. The learning of a movement conducted by a therapist holding the limb is advantageous, because the therapist has a particular sensitivity and "feeling" for the patient, which may be based on experience or on a feeling for a human body in general. In particular, the therapist can move the limb until feeling resistance due to the morphology of the patient. The therapist has an own appreciation with respect to a trajectory that may be useful to follow in the course of an exercising unit. The present invention thus allows the device of the invention to reproduce the movement that a therapeutic person may apply to a limb in the frame of human interaction-based therapeutic exercising session.

Traditionally, rehabilitation robots are fed with anthropometric data of a human subject and determine trajectories of exercises as a function of the anthropometric parameters. In this case, the function of torque and/or force measuring systems is to warrant the safe operation of the device, enabling the interruption of an exercise as soon as abnormal forces and/or torque is detected at the interface 17. However, the distinction between torque and/or force that indicates potential harm to a patient and forces/torque that can well be supported may vary from patient to patient and can generally be determined in a more accurate, personalized manner by an experienced therapist than by predetermined or calculated values used by a control unit of a rehabilitation robot. For all the foregoing reasons, the present invention, in which a movement conducted by a human assistant or therapist is "copied" by the rehabilitation robot is considered as particularly advantageous.

Preferably, the method comprises the step of entering anthropometric data of said human subject into said control unit. The human machine interface (HMI) may be used to this end.

The control unit of the exercise device preferably uses the anthropometric data of the human subject in algorithms that are run during the operation of the device. The anthropometric data may be used for a plurality of purposes. For example, anthropometric data may be used for determining trajectories of classic exercises that are predefined and not recorded in accordance with the methods of the present invention. Anthropometric data are further used for calculating further anthropometric information that is difficult to measure. For example, the weight of a limb may be calculated on the basis of the length of the limb and its part, of the circumference of the limb 1 at defined positions, such as the articulations, on the overall weight, the BMI, and based on the gender of the human subject, for example. In addition, the anthropometric data may be used for calculating the ("baseline") forces and/or torque required for maintaining a limb 1 in a fixed position in the gravity compensating mode. In general, the use anthropometric data is preferred for operating the exercise device in the frame of rehabilitation and/or therapy.

In an embodiment, the control unit 15 configured to determine a definitive, personalized exercise movement on the basis of the recorded active accompanying movement.

In an embodiment, said personalized exercise movement is determined on the basis of parameters including a trajectory, speed and acceleration of said recorded active accompanying movement. The personalized exercise movement may be a reproduction of the movement as recorded, or may be completed, adapted and/or modified by the device on the basis of the recorded movement and additional parameters.

In an embodiment of the method of the invention, said muscle-propelled movement is conducted so as to move said interface 17 away from a start position and back to a position corresponding to or close to said start position so as to form an approximate closed-loop trajectory, and wherein one or several approximate closed-loop trajectories may be conducted in said muscle-propelled movement.

In general, exercise movements conducted by exercise devices such as rehabilitation robots are conducted in a repetitive manner, so that the limb of a human subject follows the same particular, defined trajectory for several times. Therefore, the interface 17 and the limb 1 connected thereto return repetitively to a start position from which a particular trajectory can be repeated.

For the purpose of the present specification, the expression "closed-loop trajectory" refers to exercises based on repetitive movements as described above, in which the interface 17 returns to the same start position during an exercise.

In case of an exercise movement conducted by a therapist holding the limb 1 of a human subject, it is clear that the movement may not exactly be a closed looped in that the therapist may not pass at every repetition exactly through the start position. Accordingly, a human therapist holding the limb 1 and conducting a movement by acting on the limb with his her muscular force generally conducts at least one "approximate closed-loop trajectory".

Figure 3:
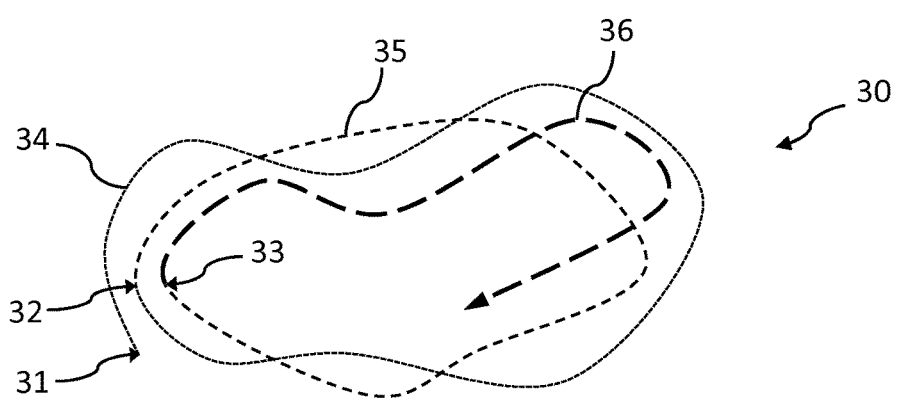
FIG. 3 schematically illustrates trajectories of muscle-propelled movements in accordance with an embodiment of the invention.

FIG. 3 illustrates trajectories 34-36 of exercise movements 30 conducted by a human assistant, such as a therapist or a doctor, for example. The dotted and dashed lines are thus the movements conducted within a plane within which a particular exercise device may provide freedom of movement. Furthermore, the lines track positions of a particular point of the interface 17, to which the limb 1 is attached, in a similar manner as FIG. 2, but not showing the orientation of the pedal 17, although the angular position of the interface 17 is preferably also part of the trajectories 34-36.

The arrow 31 indicates a start position of an exercise conducted, for example, by a human assistant holding a limb 1 in the hand. The dotted line 34 illustrates a trajectory that the interface 17 follows while accompanying the muscle-propelled movement performed by the assistant. The therapist conducts a movement which may be circular, elliptical, linear or have any trajectory leading back to the start position or to position 32 close to the start position, from which the movement is repeated. The trajectory 34 is thus an "approximate closed loop trajectory", because it does not necessarily lead back precisely to the first start position 31, but to said position 32. From arrow 32, a second movement is conducted along trajectory 35 leading to a position 33, which is again close to the start position 31 or start position 32 but not necessarily exactly identical to the start position. From position 33, a further movement is started, following trajectory 36.

For the purpose of clarification, it is mentioned that the definition of start positions 31-33 are to some extent arbitrarily made in FIG. 3, as any position on the trajectories could be in principle defined as a start position of a movement. The figure is thus used for simply illustrating the repetitive and closed-loop nature of exercises movements and/or muscle-propelled movements. FIG. 3 also illustrates that muscle-propelled movements conducted in the active compliance mode do generally not follow entirely identical trajectories. Although FIG. 3 has been illustrated with reference to a muscle-propelled movement conducted by the muscular force of a human assistant holding the limb 1 in his hand, the embodiments also apply to the situation in which a human subject moves his limb with his own muscular force.

In an embodiment of the invention, the control unit 15 determines a personalized exercise movement by calculating a definitive, closed-loop exercise movement on the basis of the recorded active accompanying movement.

In an embodiment of the invention, said muscle-propelled movement comprises one, two or more approximate closed-loop trajectories, wherein said two or more approximate closed-loop trajectories are recorded by said control unit 15 and wherein said control unit is configured to calculate an definitive closed-loop trajectory on the basis of said one, two or more recorded approximate closed-loop trajectories. Preferably, said definitive closed-loop trajectory defines or is part of said personalized exercise movement.

The control unit 15 may determine a personalized exercise movement on the basis of a single, approximate closed loop trajectory, for example by calculating a connection from the end point of the first trajectory 34 (which end point corresponds to the start point 32 of the second trajectory 35 in FIG. 3) to the start point 31 of the first trajectory.

Figure 4:
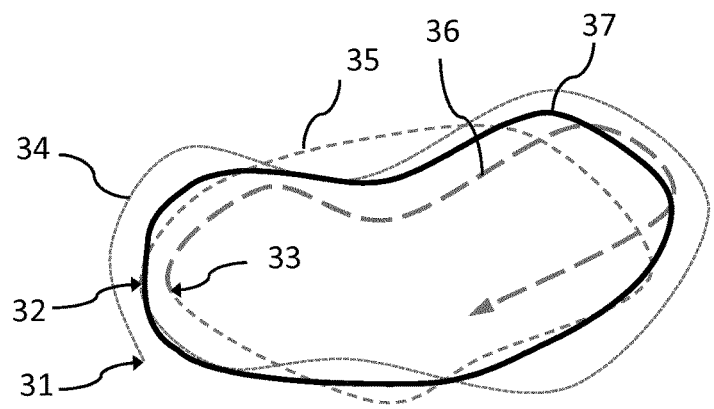
FIG. 4 schematically illustrates the determination of a personalized, closed-loop exercise movement in accordance with an embodiment of the invention.

FIG. 4 illustrates the determination of a definitive closed-loop trajectory 37 or definitive exercise trajectory 37 on the bases of exercise movements recorded in the method of the invention. The control unit 15 preferably contains algorithms for calculating a definitive exercise movement. For example, the definitive closed-loop trajectory 37 represents an average trajectory of the various trajectories 34-36 conducted during the step of conducting a muscle-propelled movement with the limb. Alternatively, the trajectory 37 of the definitive exercise movement could also follow an innermost or outermost trajectory of the trajectories 34-36 of the muscle-propelled movement. In another approach, the stored movements may simply be used for determining basic points, for example corner points of a definitive exercise movement having a different trajectory. For example, the recorded trajectories 34-36 may be used to determine the end points of a linear exercise movement, such as a movement in which the interface 17 moves back and forth along a straight line (not considering rotational movements of a pedal which will generally also be present in the case of linear movements).

The definitive closed-loop trajectory or exercise movement 37 preferably has a constant, defined trajectory. Furthermore, the definitive exercise movement is personalized, because is determined from the trajectories established with an individual human the limb of whom was attached to the device.

In an embodiment, said step of determining a personalized exercise movement on the basis of said active accompanying movement comprises calculating a closed-loop trajectory on the basis of and/or corresponding to the recorded exercise movement. The exercise device of the invention may be configured to reproduce the movements as recorded. Preferably, the exercise device is configured to determine a definitive exercise movement on the basis of the recorded movements. The definitive exercise movement can then be reproduced by the exercise device alone, without requirement of the muscular force of the human assistant 2, in the exercise mode.

In an embodiment, the invention comprises the step of modifying a movement as recorded for determining a modified exercise movement. The modified exercise movement is preferably still a personalized exercise movement. For example, the invention envisages that recorded exercise movements are modified either automatically by program codes or in accordance with inputs provided by a human operator of the device, for example via the HMI 16. On the basis of such input or on predetermined parameters in the device, it is possible to determine an exercise movement. For example, an exercise movement having the same trajectory shape but a shorter trajectory outline may be generated. This corresponds to a proportional reduction of the exercise trajectory. In another example, the extension of the trajectory along one axis only is shortened, for example along the horizontal axis, while the extension of the trajectory along the vertical axis remains as in the recorded trajectory. In an embodiment, parameters such as speed and acceleration may be modified. In summary, the device of the invention may be configured to allow the generation of modified trajectories and exercise movements on the basis of the recorded exercise movements.

In an embodiment, the exercise devise is configured to pass, in an automated manner, from a recording mode to an exercise mode. In particular, after having recorded exercise movements, such as a number of approximate closed-loop trajectories (FIG. 3), the control unit 15 is preferably configured to determine a definitive exercise movement 37 as described above with reference to FIG. 4. In a further step, the control unit switches from the active compliance mode, in which muscle-propelled movements are accompanied, to an exercise mode, in which the definitive exercise movement 37 is conducted by the exercise device propelling the motors 12 to conduct the exercise. This applies in particular to passive exercises, designed for subjects suffering from an impaired motor function.

The "switching" preferably concerns the automated change from "learning" an exercise to "reproducing" or conducting the exercise. The goal of the automated switching is that the human assistant, whose hands are occupied with holding the limbs of a human subject, does not need to push any particular button or provide any particular, separate input at the HMI 16, for example.

In an embodiment, the method of the invention comprises the step of switching, in an automated manner, from a mode in which said steps of actively accompanying said muscle-propelled movement and recording said active accompanying movement are conducted to an exercising mode, wherein, in said exercise mode, the control unit 15 actively executes said personalized exercise movement determined on the basis of said recorded active accompanying movement. In this embodiment, the movement of the interface 17 along a trajectory in the exercise mode is preferably conducted by the motors of the device. In a preferred embodiment, said personalized exercise movement is thus conducted by the device in a passive exercise mode, from the viewpoint of the human subject.

This embodiment may be described as an automated "taking-over" and/or "taking in charge" by the exercise device 3 of the exercise that is at the beginning conducted by the human assistant 2. In accordance with this embodiment, the device automatically switches from "learning" to "exercising" after the device has determined an exercise in accordance with the invention.

The exercise device 3 and in particular the control unit 15 is preferably configured to conduct a take-over according to parameters. For example, the control unit may be configured to take over the exercise after a predetermined number of approximate closed-loop trajectories conducted by the human assistant holding the limb of a human subject. According to another example, the exercise device takes over the exercise as soon as the control unit has been able to determine a definitive closed loop-trajectory from the muscle-propelled exercise movements conducted by the assistant. For example, an algorithm of the control unit 15 may require a certain number of repetitions of exercise movements conducted by the assistant, until the deviation between a calculated definitive closed-loop trajectory and the additional approximate closed loop trajectories conducted by the human assistant falls below a threshold value that triggers the control unit 15 to pass from the recording and active compliance mode to the exercising mode.

The "automated take-over" procedure may by enabled or switched on by a human assistant before starting any exercising with the human subject at the human machine interface 16 of the exercise device, for example.

The present invention encompasses that the exercise device 3 is configured to pass, in an automated manner, from the active compliance mode to a limited or trajectory fixing active compliance mode. The purpose of this embodiment is to teach the device an exercise movement in a two separate steps: In a first step, the trajectory of the exercise movement is taught, and in a second step, additional parameters of exercise movements are taught, such as speed and accelerations.

Accordingly, in an embodiment, the method of the invention comprises the steps of:
  determining a definitive exercise trajectory 37 on the basis of the recorded active accompanying movement, in particular on the basis of recorded approximate closed loop trajectories 34-36;
  fixing the definitive trajectory 37 while staying in an active compliance mode;
  recording parameters of a muscle-propelled movement conducted along the fixed, definitive trajectory 37, said parameters comprising one or more selected from speed and acceleration.

The above embodiment may be accomplished by providing two types of active compliance mode. A first active compliance mode is as described further above, in which the human assistant performs muscle propelled movements with the limb in his hand enabling the exercise device to calculate an exercise trajectory, in particular a closed loop exercise trajectory. In a subsequent step, once the control unit has determined the definitive closed-loop trajectory, the control unit is configured to switch to a limited or second active compliance movement. At this stage, the articulated system fixes or sets the definitive closed loop trajectory. It is no longer possible to conduct a movement deviating from the fixed trajectory using muscular force, but the muscle-force of the human assistant is still required to move the limb along the fixed trajectory. The articulated system 11 does thus still only move along the trajectory on the basis of force and/or torque determined from the measuring system 10.

In an embodiment, a definitive personalized exercise movement is determined by said definitive exercise trajectory and by said speed and/or acceleration parameters determined during said step of fixing the definitive exercise trajectory 37 while staying in an active compliance mode.

In the trajectory fixed active compliance mode, the control unit 15 still records parameters of the muscle propelled movements, this time in particular the speeds and accelerations. For example, the control unit may be configured to record speed and acceleration at various positions along the fixed closed loop trajectory. In this step, the human assistant holding the limb 1 can vary speed and acceleration of the muscle-propelled movement he conducts with the limb. The human assistant may thus accelerate on some parts of the trajectory and decelerate at other parts and keep constant speed at yet other parts of a trajectory. During the trajectory fixed in active compliance mode, the control unit records the speed and acceleration parameters of the articulated system while the limb is propelled by the human assistant's muscular force.

Once the assistant has conducted muscle propelled movements in the frame of the fixed closed loop trajectory, the control unit may again determine average parameters of the movement along the closed-loop trajectory as recorded during the second or limited active compliance mode. Accordingly, the method of the invention preferably comprises the step of determining a definitive exercise movement including a definitive exercise trajectory 37, speed and acceleration of an exercise movement on the basis of said recorded active accompanying trajectory and said recorded parameters.

After that, the assistant may instruct the exercise device to reproduce the exercise movement as calculated from recording in the two active compliance modes, or the exercise device may be configured in advance to automatically switch to the exercising mode in accordance with the embodiment described elsewhere in this specification.

As becomes apparent from the description of preferred embodiments and the appended claims, the invention encompasses methods in which some steps are conducted by a human assistant. In other aspects and embodiments of the method, all steps are conducted by the exercise device 3, which has been configured and programmed to perform the method steps. The steps that can be related to the teaching in the method of the invention are generally conducted by a human assistant or operator of the device, whereas the steps of learning are generally conducted by the device of the invention. In an embodiment, the step of teaching encompasses basically said step of conducting said muscle-propelled movement.

The steps of placing the human subject in an exercise position with respect to the device 3 and attaching the limb 1 of the human subject with said interface 17, and the step of conducting a muscle-propelled movement with the limb 1 are generally conducted by a human, in general the human assistant 2, but in some situation they may also be conducted by the human subject or by different assistants.

In method steps conducted by the exercise device 3, it is generally the control unit 15, which is configured to conduct the respective step. Accordingly, the control unit 15 is preferably a computer that contains various program codes that enable it to conduct the respective method steps. The various operation modes and steps conducted by the device may be programs, for example software and/or hardware units that are activated during a particular mode. Therefore, features pertaining to the method of the present invention are generally also present as program codes in the exercising device of the invention; in as far as the method step is conducted by the exercise device. For example, the steps of the measuring forces and or/torque at the interface, actively accompanying said muscle-propelled movement, recording the said active accompanying movement and determining a definitive exercise movement and/or trajectory are generally conducted by the exercise device, based on program codes and algorithms that are part of the control unit 15.

The invention claimed is:

1. A method for determining a personalized exercise movement in a computer-controlled, motorized exercise device, the device comprising a control unit, an articulated system for conducting exercise movements and one or more motors arranged to act on said articulated system under the control of said control unit, wherein said articulated system comprises an interface and an attachment arrangement for attaching the articulated system to a distal extremity of a limb of a human subject, and wherein said exercise device comprises a measuring system for determining torque and/or force at said interface, wherein the measuring system comprises one or more torque and/or force sensor directly connected at the interface, such that force and/or torque exerted by the distal extremity of the limb can be determined directly at the interface, the method comprising the steps of:
   determining forces and/or torque at said interface by way of said measuring system while a human assistant conducts a muscle-propelled movement by holding said limb of said individual human subject with the human assistant's hands while said limb acts on said interface and while said distal extremity of said limb is attached to the articulated system at said interface, wherein said human subject suffers from an impaired motor and/or sensory function of said limb;
   actively accompanying said muscle-propelled movement by said motors acting on said articulated system, wherein said control unit determines the parameters of an active accompanying movement of said articulated system on the basis of the measurements of forces and/or torque by said measuring system, wherein said step of actively accompanying said muscle-propelled movement is conducted in an active compliance mode in which said control unit determines a movement of said articulated system that is suitable to avoid occurrence of torque and/or force at said interface caused by said muscle-propelled movement;
   recording the said active accompanying movement; and
   determining a personalized exercise movement on the basis of the recorded active accompanying movement.

2. The method of claim 1, wherein a movement of the articulated system in said step of actively accompanying said muscle-propelled movement by aid of one or more motors acting on said articulated system is determined by said control unit so as to avoid resistance against said muscle-propelled movement, wherein the occurrence of resistance is determined on the basis of measurements of said measuring system.

3. The method of claim 1, wherein said control unit is configured to determine, on the basis of personal anthropometric data pertaining to said human subject and/or to the limb of said human subject, the forces and/or torque acting on said measuring system in the absence of any muscle-propelled movement while said limb is connected at said interface.

4. The method of claim 1, wherein said step of actively accompanying said muscle-propelled movement is conducted in a gravity compensating mode, in which said device supports said limb attached to said interface against the effect of gravity so as to prevent any movement of the limb caused by gravity and/or in the absence of a movement propelled by muscular force.

5. The method of claim 4, wherein said muscle-propelled movement is conducted by a human assistant holding the limb without carrying the weight of said limb, the weight of the limb being supported by the device against the effect of gravity.

6. The method of claim 1, which is conducted in a mode in which gravity of said limb is not compensated by the device, and/or wherein the weight of the limb is supported by a human assistant holding the limb and carrying the weight of the limb with his or her muscular force.

7. The method of claim 1, wherein said step of determining a personalized exercise movement on the basis of said active accompanying movement comprises calculating a closed-loop trajectory on the basis of and/or corresponding to the recorded exercise movement.

8. The method of claim 1, wherein said muscle-propelled movement comprises one, two or more approximate closed-loop trajectories, which are recorded in said step of recording said active accompanying movement, and wherein said control unit is configured to calculate a definitive closed-loop trajectory of said personalized exercise movement on the basis of said recorded approximate closed-loop trajectories.

9. The method of claim 1, wherein said step of determining a personalized exercise movement comprises the steps of:
   determining a definitive exercise trajectory on the basis of the recorded active accompanying movement;
   fixing the definitive exercise trajectory while staying in an active compliance mode; and
   recording parameters of a muscle-propelled movement conducted along the definitive trajectory, said parameters comprising one or more selected from speed and acceleration.

10. The method of claim 9, wherein said personalized exercise movement is determined by said definitive exercise trajectory and by said speed and/or acceleration parameters determined during said step of fixing the definitive exercise trajectory while staying in an active compliance mode.

11. The method of claim 1, comprising the step of switching, in an automated manner, from a mode in which said steps of actively accompanying said muscle-propelled movement and recording said active accompanying movement are conducted to an exercise mode, wherein, in said exercise mode, the control unit executes said personalized exercise movement determined on the basis of said recorded active accompanying movement.

12. The method of claim 1, wherein said measuring system for determining torque and/or force at said interface is selected from a combination of one or a plurality of sensors configured to enable the determination of force and/or torque.

13. The method of claim 1, comprising the step of conducting a muscle-propelled movement with the limb during said steps of measuring forces and/or torque at said interface.

14. The method of claim 1, comprising the step of placing the human subject in an exercise position with respect to the device and attaching the limb of the human subject with said interface before said step of actively accompanying said muscle-propelled movement.

15. The method of claim 1, wherein said exercise device comprises a human machine interface (HMI), and wherein said method comprises the step of entering anthropometric data of said human subject into said control unit.

16. The method of claim 1, wherein said exercise device is configured to compensate gravity of said articulated system so as to keep said interface at a fixed position and/or orientation in the absence of force and/or torque at said interface as determined by said measuring system for determining torque and/or force.

17. The method of claim 1, wherein said attachment arrangement comprises straps or belts.

18. A computer-controlled, motorized exercise device comprising:
   one or more motors;
   an articulated system for conducting movements under the activity of said motors, the articulated system comprising at least one interface and an attachment arrangement for attaching said articulated system to a distal extremity of a limb of a human subject, said human subject suffering from an impaired motor or sensory function of said limb;
   a measuring system comprising one or more torque and/or force sensor directly connected at the interface, said measuring system being configured to measure torque and/or forces generated at said interface by the distal extremity of said limb of said human subject while a human assistant conducts a muscle-propelled movement by holding said limb of said human subject with the human assistant's hands;
   a control unit configured to control a movement of said articulated system by controlling said one or motors;
   wherein said control unit is configured to operate in a mode of active compliance for actively accompanying said muscle-propelled movement by said motors acting on said articulated system while said distal extremity of said limb is attached to the articulated system at said interface, wherein, in said mode of active compliance, said control unit determines parameters of an active accompanying movement of said articulated system on the basis of forces and/or torque measured by said measuring system, wherein said active accompanying movement is suitable to avoid occurrence of torque and/or force at said interface caused by said muscle-propelled movement, and;
   wherein said computer-controlled, motorized exercise device is further configured to record said active accompanying movement in said mode of active compliance and to determine a personalized exercise movement on the basis of the recorded active accompanying movement.

19. The device of claim 18, wherein said control unit is configured to conduct said accompanying movement by:
   measuring forces and/or torque by said torque and/or force sensor;
   determining the extent to which said force and/or torque are caused by a muscle-propelled movement of said limb;
   determining a movement and/or new position of the interface that is suitable to avoid force and/or torque caused by the muscle-propelled movement at the interface; send instructions to the motors so as to cause the articulated system to conduct said movement suitable to avoid force and/or torque caused by the muscle-propelled movement, thereby actively accompanying said muscle-propelled movement.

20. The device of claim 18, wherein said control unit is configured to actively produce said personalized exercise movement in an exercise mode.

* * * * *